United States Patent [19]

McClune et al.

[11] Patent Number: 5,024,935

[45] Date of Patent: Jun. 18, 1991

[54] DYE-PROVIDING COMPOSITION, DIAGNOSTIC TEST KIT AND THEIR USE IN METHOD FOR LIGAND DETERMINATION USING PEROXIDASE LABELED-RECEPTOR

[75] Inventors: Gregory J. McClune; John F. Bishop, both of Rochester, N.Y.

[73] Assignee: Eastman Kodak Company, Rochester, N.Y.

[21] Appl. No.: 136,166

[22] Filed: Dec. 18, 1987

[51] Int. Cl.$^5$ .................. G01N 33/53; G01N 33/536; C12Q 1/28; C12N 9/96

[52] U.S. Cl. ...................................... 435/7.1; 435/7.5; 435/7.9; 435/7.92; 435/7.94; 435/28; 435/188; 435/180; 435/810; 436/501; 436/518; 436/536; 436/538; 436/543; 436/547; 436/808; 436/818; 436/824; 526/246; 526/303.1; 526/317.1; 528/422; 528/425; 548/346

[58] Field of Search ............. 435/7, 18, 27, 28, 77, 435/180, 810, 188, 7.1, 7.5, 7.9, 7.92, 7.94; 436/501, 518, 527–530, 800, 808, 823, 824, 818; 526/264, 303.1, 317; 528/422, 425; 548/346

[56] References Cited

U.S. PATENT DOCUMENTS

| | | | |
|---|---|---|---|
| 4,089,747 | 5/1978 | Bruschi | 195/99 |
| 4,184,923 | 1/1980 | Schubert | 435/25 |
| 4,228,259 | 10/1980 | Kalopissis et al. | 528/336 |
| 4,277,437 | 7/1981 | Maggio | 436/537 |
| 4,283,491 | 8/1981 | Dappen | 435/10 |
| 4,434,150 | 2/1984 | Azad et al. | 424/1.1 |
| 4,478,942 | 10/1984 | Katsugama et al. | 436/135 |
| 4,478,944 | 10/1984 | Gross et al. | 436/95 |
| 4,496,654 | 1/1985 | Katz et al. | 435/7 |
| 4,503,143 | 3/1985 | Gerber et al. | 435/7 |
| 4,596,770 | 6/1986 | Parham et al. | 435/7 |
| 4,670,385 | 6/1987 | Babb et al. | 435/28 |
| 4,746,607 | 5/1988 | Mura et al. | 435/25 |
| 4,788,140 | 11/1988 | Findlay et al. | 435/17 |
| 4,806,450 | 2/1989 | Hofmann et al. | 430/281 |
| 4,820,490 | 4/1989 | Morris | 436/805 |
| 4,828,983 | 5/1989 | McClune | 435/7 |
| 4,870,007 | 9/1989 | Smith-Lewis | 435/28 |
| 4,874,692 | 10/1989 | Eikenberry | 435/7 |

FOREIGN PATENT DOCUMENTS

| | | |
|---|---|---|
| 0038205 | 10/1981 | European Pat. Off. . |
| 0122641 | 10/1984 | European Pat. Off. . |
| 0256562 | 2/1988 | European Pat. Off. . |
| 3411997 | 10/1985 | Fed. Rep. of Germany . |
| 58-45557 | 3/1983 | Japan . |
| 85-02018 | 5/1985 | PCT Int'l Appl. . |

OTHER PUBLICATIONS

Cumbo et al, Chemical Abstracts, vol. 105, Abstract No. 3065x, 1986.
Chemical Abstracts, vol. 89, Abstract No. 103037j, 1978.
Chemical Abstracts, vol. 87, Abstract No. 163689s, 1972.
Fukuoka et al, Chemical Abstracts, vol. 67, Abstract No. 82717j, 1967.

*Primary Examiner*—Esther L. Kepplinger
*Assistant Examiner*—Florina B. Hoffer
*Attorney, Agent, or Firm*—J. Lanny Tucker

[57] ABSTRACT

A dye-providing composition comprises a water-soluble or -dispersible polymer, such as a vinylpyrrolidone polymer, and an imidazole leuco dye capable of providing a dye in the presence of hydrogen peroxide and a peroxidative substance. The weight ratio of polymer to leuco dye is from about 10,000:1 to about 100:1. The dye-providing composition can be included with a peroxidase substrate in a diagnostic test kit. A method for the determination of a ligand can be carried out using a peroxidase labeled-receptor for the ligand and the dye-providing composition described above. The method is particularly useful for the determination of human chorionic gonadotropin (hCG).

21 Claims, No Drawings

DYE-PROVIDING COMPOSITION, DIAGNOSTIC TEST KIT AND THEIR USE IN METHOD FOR LIGAND DETERMINATION USING PEROXIDASE LABELED-RECEPTOR

FIELD OF THE INVENTION

The present invention relates to a dye-providing composition comprising an imidazole leuco dye that provides a dye in the presence of hydrogen peroxide and a peroxidative substance, such as peroxidase. It also relates to a test kit including this composition and to a ligand-determining method using the dye-providing composition and a peroxidase-labeled receptor for the ligand.

BACKGROUND OF THE INVENTION

There is a continuous need in medical practice, research and diagnostic procedures for rapid and accurate determinations of biological substances which are present in biological fluids at low concentrations. For example, the presence of drugs, narcotics, hormones, steroids, polypeptides, prostaglandins or infectious organisms in blood, urine, saliva, vaginal secretions, seminal fluids and other biological fluids has to be determined in an accurate and rapid fashion for suitable diagnosis or treatment.

To provide such determinations, various methods have been devised for isolating and identifying biological substances employing specific binding reactions between the substance to be detected (identified as a "ligand" herein) and receptors specifically reactive with that substance. Radioactive, fluorescent or enzyme labels have been used to detect the resulting reactive complex.

In recent years, the use of enzyme labels has received increasing attention because of various advantages over the use of radioactive and fluorescent labels. Assays using enzyme labels include what are known in the art as competitive enzyme immunoassays (EIA) and both direct and indirect enzyme linked immunosorbent assays (ELISA).

Another type of assay which has been developed is what is known in the art as an immunometric or a "sandwich" assay. Such an assay involves "sandwiching" the ligand (such as an antigen) with two or more receptor molecules (such as antibodies) which complex with the compound in a non-interfering manner and at different epitopic sites. Examples of such assays are described in U.S. Pat. No. 4,486,530 (issued Dec. 4, 1984 to David et al) where monoclonal antibodies having high affinity are used. In most sandwich assays, one or more of the receptor molecules are suitably immobilized on an insoluble carrier such as small particles, membranes, plates, or similar objects, and another receptor is suitable labeled, such as with an enzyme.

Peroxidase is one enzyme which has been used as a label in various assays, including specific binding assays of all types. Peroxidase acts on hydrogen peroxide as a substrate and can oxidize various chromogens or dye-providing materials to provide a detectable species in proportion to the amount of peroxidase present. Various dye-providing materials are known in the art, including benzidine and derivatives thereof. Such materials are described in U.S. Pat. Nos. 4,503,143 (issued Mar. 5, 1985 to Gerber et al) and 4,596,770 (issued June 24, 1986 to Parham et al).

In the latter reference, tetraalkylbenzidines are used in N-methylpyrrolidone as a dye-providing composition with peroxidase labeled antibodies in immunoassays. While such compositions may be useful if prepared and used immediately in a solution assay, it has been found that use of tetraalkylbenzidines provide insufficient sensitivity in certain assays where the ligand is present in the test fluid in low concentrations. Also the benzidine compositions are relatively unstable. In addition, in certain assays carried out using filter membranes, the membranes must be pretreated because the dye obtained from tetraalkylbenzidines, such as tetramethylbenzidine, is water-soluble and would otherwise pass through the membrane inadvertently.

It would be useful to have a more stable dye-providing composition which can be packaged into kit form for lengthy storage. It would also be desired to have a more sensitive diagnostic method which could be sold for use in various environments, including doctors' offices and in a consumer's home.

SUMMARY OF THE INVENTION

The problems noted above are overcome with a dye-providing composition comprising a water-soluble or -dispersible polymer, and an imidazole leuco dye capable of providing a dye in the presence of hydrogen peroxide and a peroxidative substance, the weight ratio of polymer to leuco dye being from about 10,000:1 to about 100:1, and the polymer is selected from the group consisting of vinylpyrrolidone polymers, acrylamide polymers, acrylic and methacrylic acid polymers, polyethylene glycols and polyamines.

Also provided with this invention is a diagnostic test kit for the determination of an analyte as a result of the catalytic activity of peroxidase, the kit comprising:

(a) a substrate for peroxidase, and (b) the dye-providing composition described above.

Further, a method for the determination of a ligand in an aqueous liquid comprises:

A. contacting a sample of the liquid with a peroxidase labeled-receptor for the ligand to form a reaction product of the ligand with the receptor, B. prior to, simultaneously with or subsequently to the contacting step (A), contacting the liquid sample with the dye-providing composition described above, C. separating the reaction product from unreacted materials, and D. determining the presence or absence of the reaction product.

The present invention provides a greatly improved dye-providing composition that can be used to advantage where peroxidase or another peroxidative substance is involved in an assay. This dye-providing composition has improved stability because of the combination of a particular water-soluble or -dispersible polymer with an imidazole leuco dye which is oxidized to a dye in the presence of hydrogen peroxide and a peroxidative substance, such as peroxidase.

This dye-providing composition can be readily packaged into a diagnostic test kit which can be transported and stored for extended periods of time without significant loss in sensitivity. Very low levels of peroxidase labeled specific binding compounds can be detected with this invention because of the high sensitivity of the dye-providing composition.

In preferred embodiments where an assay is performed using a filter membrane, for example in a disposable test device, the membrane does not have to be pretreated in contrast to when tetramethylbenzidine is used as the dye-providing material. Surprisingly, the polymer in the composition of this invention facilitates keeping the imidazole leuco dye in solution in the dye-providing composition and facilitates immobilization of the resulting dye on the membrane during the assay. While not wanting to be limited to a mechanism for the advantages achieved with the present invention, it is believed that the polymer and leuco dye may form a complex of some type. This complex is then kept in solution by the polymer.

DETAILED DESCRIPTION OF THE INVENTION

The composition of the present invention is useful for providing a dye in the presence of a peroxidative substance, such as peroxidase, and hydrogen peroxide. The composition can be used in the determination of hydrogen peroxide or peroxidase, or any analyte which is capable of reacting, in one or more reactions, to produce hydrogen peroxide. For example, it can be used to advantage in assays for such analytes as glucose, galactose, amino acids, uric acid, triglycerides, creatine kinase (total or isoenzymes thereof), cholesterol and others known in the art where peroxidase is used in a sequence of reactions to produce a detectable species as a result of the presence of the analyte. Preferably, the composition of this invention is used in assays which involve specific binding reactions, such as immunoassays, as described in more detail below.

The composition includes one or more water-soluble or -dispersible polymers, such as vinyl pyrrolidone polymers, acrylamide polymers, acrylic and methacrylic acid polymers, polyethylene glycols and polyamines. These polymers can be either homo- or copolymers. Representative examples of useful polymers include, but are not limited to: poly(acrylic acid), poly(methacrylic acid), poly(acrylic acid-co-methyl acrylate) (90:10 weight ratio), poly(acrylamide), poly(acrylamide-co-acrylic acid) (50:50 weight ratio), polyamines such as those described in U.S. Pat. Nos. 3,702,249 and 4,689,359. Particularly useful polymers are vinyl pyrrolidone polymers, that is a homo- or copolymer prepared from vinylpyrrolidone such as poly(vinylpyrrolidone), poly(vinylpyrrolidone-co-acrylic acid) and poly(vinylpyrrolidone-co-acrylamide). These polymers facilitate in keeping the leuco dye in aqueous solution, as well as facilitating the immobilization of the resulting dye onto substrates, such as filter membranes, without the need to pretreat the membrane.

The polymers can also contain minor amounts (that is, less than 50 molar percent) of other ethylenically unsaturated polymerizable monomers which do not interfere with the function of the invention, or with the leuco dye. Poly(vinylpyrrolidone) is a preferred polymer.

The composition of this invention also includes one or more leuco dyes which are capable of providing a dye in the presence of hydrogen peroxide and a peroxidative substance. The resulting dye is generally detectable in the visible region of the electromagnetic spectrum (generally from about 400 to about 700 nm). Preferably, the dye is detected at from about 500 to about 650 nm.

Imidazole leuco dyes useful herein are either diarylimidazole or triarylimidazole leuco dyes. Many useful compounds are known in the art, including those described in U.S. Pat. No. 4,089,747 (issued May 16, 1978 to Bruschi) and references noted therein, E.P. Publication No. 122,641 (published Oct. 24, 1984) and Japanese Patent Publication No. 58(1983)-045,557.

The triarylimidazoles having the following general formula are particularly useful:

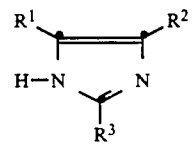

wherein $R^1$, $R^2$ and $R^3$ are each an organic group such that at least one of them is an ortho- or para-hydroxy substituted aryl group of up to 18 carbon atoms, the other two groups being aryl groups chosen such that the imidazole oxidation potential is between about $-70$ and $+110$ mV as measured by cyclic voltammetry against a standard calomel electrode using a carbon based electrode. Oxidation potential measurements can be made according to conventional electrochemical techniques (see, for example, Sawyer et al, *Experimental Electrochemistry for Chemists*, John Wiley & Sons, New York, 1974).

As used herein, the term "aryl" is meant to include aromatic hydrocarbon groups, such as phenyl, naphthyl or anthryl, tolyl, xylyl and other substituted aromatic groups. The number of carbon atoms refers to the total number of nuclear carbon atoms as well as those in substituents. At least one of the $R^1$, $R^2$ and $R^3$ groups has an ortho or para electron donating substituent such as an alkyloxy (—OR) wherein R is alkyl of 1 to 8 carbon atoms (for example, methyl, ethyl, isopropyl, t-butyl, hexyl, chloromethyl or methoxymethyl), or a dialkylamino wherein alkyl is as just defined. The $R^1$, $R^2$ and $R^3$ groups can have one or more other substituents which are electronically compatible with the imidazole nucleus to provide a suitable dye upon oxidation. Further details of preferred triarylimidazole compounds and methods of preparing them are found in U.S. Pat. No. 4,089,747 noted above.

Particularly useful triarylimidazole leuco dyes are selected from the group consisting of:

2-(4-hydroxy-3,5-dimethoxyphenyl)-4,5-bis(4-methoxyphenyl)imidazole, 2-(3,5-dibromo-4-hydroxyphenyl)-4,5-diphenylimidazole, 2-(3-bromo-5-methoxy-4-hydroxyphenyl)-4,5-bis(4-methoxyphenyl)imidazole, 4,5-bis(4-dimethylaminophenyl)-2-(4-hydroxyphenyl)imidazole, 4,5-bis(4-dimethylaminophenyl)-2-(4-hydroxy-3-methoxyphenyl)imidazole, 2-(4-hydroxyphenyl)-4,5-bis(4-methoxyphenyl)imidazole, and 4,5-bis(4-dimethylaminophenyl)-2-(4-hydroxy)-3,5-dimethoxyphenylimidazole.

The amounts of leuco dye and polymer in the composition can be varied widely depending upon how the composition is used. Generally, the leuco dye is present in an amount of from about $10^{-6}$ to about $10^{-3}$ and preferably from about $10^{-5}$ to about $10^{-4}$ molar. The polymer amount depends upon the amount of leuco dye used. Generally, the weight ratio of polymer to leuco dye is generally from about 10,000:1 to about 100:1, and preferably from about 5,000:1 to about 500:1, in order to achieve the advantages described above.

The components of the composition described above are readily available commercially from a number of sources. Alternatively, they can be prepared using known starting materials and procedures, as described in U.S. Pat. No. 4,089,747 and other references noted above.

The composition is generally in an aqueous medium although in one embodiment, minor amounts of water-miscible organic solvents can be included to solubilize the leuco dyes or other hydrophobic reagents. Methanol or other alcohols, acetone or acetonitrile are useful in this manner. Preferably, the leuco dye is dissolved directly within an aqueous solution of the polymer.

The compositions can also include other components as needed for a particular use. For example, the composition can also include either hydrogen peroxide or a peroxidative substance, but not both because the leuco dye would then be prematurely oxidized. Peroxidative substances are those capable of catalyzing the oxidation of another substance by means of hydrogen peroxide or other peroxides. Such substances include, but are not limited to, natural and synthetic peroxidases, cytochromes, hemin, forms of hemoglobin, alkaline hematin, iron sulfocyanate, iron tannate, chromic salts and the like. Peroxidase is a particularly useful peroxidative substance.

The composition can also include a specific binding compound which is attached to a peroxidative substance, such as a peroxidase-labeled immunologically reactive compound. A specific binding compound is a chemical or biological substance which will react specifically with another compound, such as avidin with biotin, or an antibody with its corresponding antigen. These materials are described in more detail below.

Electron transfer agents, that is compounds which facilitate the transfer of one or more electrons between compounds in oxidation-reduction reactions, can also be included in the composition. Many useful electron transfer agents are known in the art, such as phenazine methosulfate, benzo- and naphthoquinones as described in U.S. Pat. No. 4,746,607, issued May 24, 1988 to Mura et al. Particularly useful electron transfer agents are the phenols and anilines described in U.S. Pat. No. 4,828,983 (issued May 9, 1989 to McClune).

Buffers and chelating agents can also be optionally included in the composition of this invention.

A preferred composition of this invention is buffered to a pH of from about 6 to about 8 and comprises hydrogen peroxide, a phenolic electron transfer agent, poly(vinylpyrrolidone) and a triarylimidazole leuco dye chosen from the list of preferred leuco dyes shown above with 2-(4-hydroxy-3,5-dimethoxyphenyl)-4,5-bis(4-methoxyphenyl)imidazole being most preferred.

A diagnostic test kit of this invention includes the composition described above as well as one or more other reagents, test devices or utensils for an assay. The kit includes a substrate for peroxidase, that is, a suitable peroxide, such as hydrogen peroxide.

Preferably, the kit also includes a test device for performing an assay, such as an immunoassay. Such a test device generally comprises a water-insoluble substrate having one or more test zones (such as test wells). The substrate is prepared from a water-insoluble material such as glass, polymeric materials, cellulosic materials and other materials known in the art. The device can be a test tube, petri dish, filter paper or test strip having the zones for reaction. It can also be a microtest plate having a multiplicity of preformed test wells. Particularly useful test devices are described in U.S. Pat. No. 4,870,007 (issued Sept. 26, 1989 to Smith-Lewis).

The kit can also contain one or more of the following: a water-insoluble separation specific binding reagent which insolubilizes another compound by reaction specifically with it and separates it from other materials, peroxidase labeled-specific binding compounds (such as peroxidase labeled-antibodies), wash solutions, biotinylated antibodies, buffer solutions, reagent solutions, bottles, pipettes, test devices, prefilter devices, and other materials known to be useful in diagnostic kits to facilitate assays. Many of these optional materials are described in more detail in U.S. Pat. No. 4,870,007, noted above, and in copending and commonly assigned U.S. Ser. No. 136,165 filed on even date herewith by Sutton et al and entitled "Avidin- and Biotin-Immobilized Reagents, Analytical Elements and Methods of Use", now abandoned in favor of C.I.P. U.S. Ser. No. 315,086, filed May 16, 1989."

The present invention provides a method whereby a detectable complex between a ligand (a substance to be detected) and a receptor (a compound which reacts specifically with the ligand) is obtained. Advantageously, the method is simple and therefore can be performed in a doctor's office or in a consumer's home to provide immediate results. The test can be used to detect the presence or absence of a mono- or multivalent or multideterminant ligand in an aqueous liquid, such as a biological fluid. Preferably, it is used to detect a multideterminant ligand, such as hCG.

A monovalent ligand has a single epitopic site for complexation. A multivalent ligand has two or more epitopic sites for complexing with a multiplicity of the same specific binding receptor. A multideterminant ligand has two or more epitopic sites for complexing with a multiplicity of different receptors.

More specifically, the present invention can be used in the determination (qualitative or quantitative measurement) of a ligand in aqueous liquids to which there are naturally occurring or synthetically produced specific binding receptors. This determination can be made by merely determining the presence or absence of the ligand, or by quantitatively determining the amount of ligand. In particular, the invention can be used to assay biological fluids of animals, humans or plants, but preferably of humans. Such fluids include, but are not limited to, whole blood, plasma, sera, lymph, bile, urine, spinal fluid, seminal fluid, lacrimal fluid, vaginal secretions, sputum, perspiration and the like as well as stool specimens. It is also possible to assay fluid preparations of human or animal tissue such as skeletal muscle, heart, kidney, lungs, brains, bone marrow, skin and the like.

The ligand of interest can be an immunological species which is (1) any substance which, when presented to an immunocompetent host, will result in the production of a specific antibody capable of binding with that substance, or (2) the antibody so produced, which ligand participates in an antigen-antibody reaction. In some embodiments, avidin, biotin or an avidin or biotin derivative, or an enzyme or other label is suitably attached to the receptor molecule which reacts specifically with the ligand.

Representative ligands detectable with the present invention include primary amines, amino acids, peptides, polypeptides, proteins, lipoproteins, glycoproteins, drugs, haptens, enzymes, steroids, lipids, nucleic acids, hormones, vitamins, polysaccharides, glycolipids, alkaloids, organisms (bacteria, protozoa, fungi, viruses including retroviruses, rickettsia and the like) and components thereof, blood components, tissue and organ antigens and other materials known to one skilled in the art. In some instances, the ligand is an antibody which is directed against a drug, hormone, antibiotic or other compound having antigenic properties. Alternatively, the ligand can be an antigenic material. In still another embodiment, the immunological species is an antibody which is directed against another antibody (that is, an anti-antibody). Both monoclonal and polyclonal antibodies can be used, and they can be whole molecules or various fragments thereof. Preferably, monoclonal antibodies are used in the assays.

In a preferred embodiment, the method is useful for the detection of hCG as an early indicator of pregnancy. In this embodiment, one or more different antibodies to hCG are immobilized in the test device in order to provide reagents for forming a complex with hCG at different epitopic sites. This embodiment is described in more detail in U.S. Pat. No. 4,870,007 noted above.

Generally, the method of this invention is carried out by contacting a peroxidase labeled-receptor for a ligand of interest with a sample of liquid suspected of containing the ligand in such a manner as to form a reaction product of any ligand present and the receptor in the test device. Generally, the liquid sample is applied to a test zone of a test device or placed in a test well, depending upon the configuration of the device. The presence or absence of the reaction product is then determined in a suitable manner after contact with the dye-providing composition of this invention and separation of the reaction product from unreacted materials.

The method of the invention can be a competitive binding immunoassay using both labeled and unlabeled receptor. Either bound (that is, complexed) or unbound (that is, uncomplexed) materials can be determined. Physical separation of bound and unbound materials, if desired, can be carried out using any suitable separation technique.

In a preferred embodiment, the method is what is known in the art as an immunometric assay. The details of such assays are provided in U.S. Pat. No. 4,486,530 (issued Dec. 4, 1984 to David et al). Such an assay can be used to to determine multivalent or multideterminant ligands as described above, that is having two or more epitopic sites for immunological reaction with two or more receptor molecules. In the sandwich assay, a second receptor is brought into contact with the ligand either prior to, simultaneously with or subsequent to contact of the ligand with the test device (and hence, contact of the ligand with the first receptor). The result is the formation of a complex of the two distinct receptors with the ligand. Preferably, at least one of the receptors is biotinylated. Most preferably, the first receptor is biotinylated. The resulting complex is insolubilized when the avidin on an insoluble phase and biotin as part of the first receptor react, and the resulting insolubilized complex can be separated from unreacted material in the test device. One of the receptors or the insoluble phase can be labeled suitably for detection of the insolubilized complex.

In a preferred embodiment, a method for the determination of hCG in an aqueous liquid comprises the steps of:

A. contacting a sample of the liquid with a test device comprising a water-insoluble substrate having one or more test zones, and having immobilized in at least one of the test zones, a biotinylated antibody to hCG which is in dry form and admixed with one or more dried, water-soluble polymeric binder materials, to form a reaction product of hCG with the biotinylated antibody at a first epitopic site, B. prior to, simultaneously with or subsequent to the contacting step (A), contacting the liquid sample with a second antibody to hCG which is labeled and which reacts with hCG at a second epitopic site, to form a complex of hCG with the first and second antibodies, C. contacting the complex with an insolubilizing separation specific reagent comprising an insoluble phase to which avidin is bound, to form an insolubilized complex through reaction of avidin with biotin, D. prior to, simultaneously with or subsequent to the contacting step (C), contacting the complex with the dye-providing composition described herein while in the presence of hydrogen peroxide, E. separating the resulting labeled, insolubilized complex from unreacted materials, and F. determining the presence or absence of the labeled, insolubilized complex by measuring the amount of dye associated with the complex.

This method can be practiced in a doctor's office or at home for early determination of pregnancy by assaying urine samples.

The following examples are representative of the practice of this invention and is not intended to limit the scope of the invention.

MATERIALS

MOPS buffer is 3-(N-morpholine)propanesulfonic acid (pH 7.5), and avidin were both obtained from Sigma Chemicals Co.

TWEEN 20 is a polyoxyethylene sorbitan monolaurate nonionic surfactant available from ICI Americas, Inc.

PVP is poly(1-vinyl-2-pyrrolidone) (MW=40,000) which was obtained from GAF Chemical Corp.

Human chorionic gonadotropin was obtained from Calbiochem.

A biotinylated antibody was prepared using monoclonal anti-hCG antibodies purchased from Immuno-Search, Inc. and biotin N-hydroxysuccinimide purchased from Calbiochem-Behring Corp. following the procedure described by Hofmann et al, *J. A. C. S.* 100, p. 3585 (1978).

The peroxidase-labeled antibody was prepared using monoclonal anti-hCG antibodies purchased from Cambridge Medical Diagnostics and horseradish peroxidase purchased from Miles, Inc. following the procedure described by Yoshitake et al, *Eur. J. Biochem.*, 101, p. 395 (1979).

Succinylated casein was prepared by reacting casein with an equal weight of succinic anhydride for four hours at 25° C., then purifying the product by dialysis.

Other materials used in the examples were obtained from Eastman Kodak Co. or Sigma Chemical Co.

EXAMPLE 1

Dye-Providing Composition Useful for the Determination of Leutinizing Hormone The following dye-providing composition is useful in the determination of LH in the practice of this invention.

A solution of 4,5-bis(4-methoxyphenyl)-2-(3,4-dimethoxy-4-hydroxy)imidazole leuco dye in methanol (15 mg/ml) was prepared. A sample of this solution (5 ml) was added to 500 ml of a solution comprising sodium dihydrogen phosphate (100 mmolar, pH 7), polyvinyl pyrrolidone (1%), diethylenetriaminepentaacetic acid chelating agent (5 mmolar), hydrogen peroxide (5 mmolar) and 4'-hydroxyacetanilide electron transfer agent (5 mmolar) which had been adjusted to pH 7 using sodium hydroxide.

EXAMPLE 2

Dye-Providing Composition Useful for the Determination of hCG

The following composition was prepared and used for the determination of hCG according to the practice of the present invention.

A first aqueous solution was prepared with sodium dihydrogen phosphate (10 mmolar), diethylenetriaminepentaacetic acid chelating agent (10 $\mu$molar) and 4'-hydroxyacetanilide electron transfer agent (5 mmolar). This solution was adjusted to pH 6.8 with 10 molar sodium hydroxide.

A second aqueous solution was prepared with 20% (w/w) polyvinylpyrrolidone and 0.01% of the leuco dye of Example 1.

One part by weight of the second solution was added to nineteen parts of the first solution. Hydrogen peroxide (30%, 9.7 molar) was added to produce a final concentration of 10 mmolar hydrogen peroxide.

EXAMPLE 3

Assay of Urine for hCG Preparation of Insolubilizing Reagent

The following procedure for attachment of avidin to an insoluble phase is taken from Example 1 of U.S. Ser. No. 136,165 of Sutton et al, noted above.

The three solutions outlined below were continuously added to a 1365 ml vessel containing deoxygenated water at 80° C. at the indicated rates:

Solution 1: Styrene (739 g), m and p-(2-chloroethylsulfonylmethyl)styrene (82 g) and 1-dodecanethiol (8.2 g) at 2.5 g/min. for 380 minutes.

Solution 2: Ammonium persulfate (19.7 g) and distilled, deoxygenated water (1152 g) at 2.14 g/min. for 380 minutes.

Solution 3: Sodium pyrosulfite (9.9 g) and distilled water (1152 g) at 2.27 g/min. for 380 minutes.

After 380 minutes, the reaction was stopped, yielding about 1218 g of latex at 33.4% solids. The latex was dialyzed for 3 days to yield a latex having 27.3% solids and a pH of 5. This latex was diluted to 13.5% solids. NMR analysis confirmed a 96:4 molar ratio of styrene to the second monomer. The resulting latex particles had an average diameter of about 0.67 $\mu$m as measured by transmission electron microscopy.

A sample (0.75 ml) of the latex described above was diluted to 20 ml with borate buffer (50 mmolar, pH 8.5) and avidin (5 mg) was subsequently added. The resulting suspension was agitated in an end-over-end fashion at 37° C. for 18 hours, followed by centrifugation. The supernatant was discarded and the particles washed once with buffer by centrifugation and resuspended in 10 ml borate buffer. Biotin binding analysis (that is, titration with tritium labeled biotin) indicated that avidin had been covalently attached to the particles ($7 \times 10^{-6}$ molar binding sites per 0.3% bead suspension) to form a reagent of the present invention.

A test device as described in copending and commonly assigned U.S. Ser. No. 98,248, filed Sept. 18, 1987 by Hinckley et al was used to determine hCG in a urine sample in the following manner. This device contained three test wells each having a filter membrane consisting of a commercially available nylon membrane coated with succinylated casein (1.07 g/m$^2$).

A negative control test well of the test device contained MOPS buffer (2 mg) in polyacrylamide binder (60 $\mu$g). The test sample well contained biotinylated anti-hCG antibodies (3 $\mu$g) immobilized therein with polyacrylamide binder (60 $\mu$g), and MOPS buffer incorporated therein in a separate location. A positive control test well contained biotinylated anti-hCG antibodies (3 $\mu$g) in polyacrylamide binder (60 $\mu$g), MOPS buffer (2 mg) in a separate location therein and hCG (400 mI.U.).

A urine specimen, prefiltered to remove impurities, and containing about 50 mI.U./ml of hCG was added to each well of the test devices, followed by addition of peroxidase-labelel anti-hCG antibodies (40 $\mu$l of a $10^{-9}$ molar solution). After a one minute incubation, the insolubiling reagent described above was added (40 $\mu$l of 0.42% dispersion) to each well and the fluid was allowed to drain through the membrane in each well.

A wash solution comprising 200 $\mu$l of sodium phosphate (0.1 molar) was sodium dodecylsulfate (10 mmolar).

A leuco dye solution (40 $\mu$l) described in Example 2 was then added to each test well. After two minutes, the color that was formed on the membrane in each well was measured using conventional reflectance equipment and procedures, and converted to transmittance density using the Williams-Clapper transform. The amount of dye measured was an indication of the amount of hCG in the urine specimen tested.

EXAMPLE 4

Assay for Leutinizing Hormone (LH)

This example was taken from U.S. Ser. No. 136,165 of Sutton et al, noted above. It demonstrates the use of the dye-providing composition of this invention in an assay for LH.

Immobilization of Avidin on Particles

A solution (50 ml, 0.05 molar, pH 8.5) of borate buffer containing thiomersal (0.01%) was placed in a polypropylene centrifuge tube, and to it was added 6 ml of a solution of egg white avidin (6 mg, Sigma Chemical Co.) dissolved in 6 ml of deionized distilled water. The tube was then capped and shaken vigorously, followed by addition of 1.35 ml of a dispersion (15.5% solids) of poly[styrene-co-m and p-(2-chloroethylsulfonylmethyl)styrene] (95.5:4.5 molar ratio) beads (average size of 2.54 micrometers) and rotation end-over-end for 24 hours.

The polymer beads having avidin covalently attached thereto were washed with glycine buffer (0.1 molar, pH 8.5) containing 0.01% thiomersal, and then resuspended in glycine buffer (0.1 molar) containing 0.01% thiomersal to produce a dispersion containing an insoluble separation specific binding reagent (0.3% solids).

Assay for LH

A test device having three test wells like that described in Example 3 having a 5 μm nylon filter membrane in each well which had been pretreated with casein, was used in this assay. Also used in the assay were: a biotinylated antibody to LH (0.044 mg/ml in phosphate buffered saline solution) prepared similarly to the biotinylated antibody to hCG described above, a horseradish peroxidase labeled antibody to LH (0.0015 mg/ml in phosphate buffered saline solution containing 0.5% bovine serum albumin), and the reagent described above comprising avidin on beads (0.9% solids, pH 8.5).

Several urine samples were tested in this assay:

(a) a sample collected the 13th day of a woman's menstrual cycle containing 18 mIU LH/ml, and (b) a sample collected the 14th day of the the woman's menstrual cycle containing 64 mIU LH/ml.

Both of these samples were taken from the same person and the LH content was determined by an LH radioimmunoassay kit available from Diagnostic Products Corporation.

A mixture of urine sample (a) (200 ml), the peroxidase-labeled antibody (35 ml) and the biotinylated antibody (10 ml) was prepared and incubated at room temperature for two minutes. The insolubilized avidin reagent (40 ml) was then added to the mixture and incubation was continued for another five minutes. The mixture was then transferred to one of the test wells of the test device, and fluid and unreacted materials were drained away leaving insolubilized complex formed during incubation on the filter membrane. The remaining insolubilized product was then washed twice with phosphate buffered saline solution (125 ml) containing 0.1% TWEEN 20 surfactant, filtered again and then contacted with the dye-providing composition of Example 1 (50 μl).

Urine sample (b) was simlilarly assayed using a second test well of the test device.

In both test wells, a color was seen on the filter membrane within five minutes. The color in the first well was light pink in color whereas the color in the second well was bright red in color.

EXAMPLE 5

ELISA Determination of Streptococcus A Antigen After Extraction with Citric Acid This example illustrates the detection of Streptococcus A antigen using an ELISA (Enzyme Linked Immunosorbent Assay) method. It is taken from U.S. Ser. No. 98,431 filed by Snyder et al Sept. 18, 1987, but the leuco dye composition described therein is our invention.

An isolate of Streptococcus A (20 μl), obtained from a local hospital, was treated to extract antigen for one minute at 25° C. using a solution of sodium nitrite (8 molar, 120 μl) and citric acid (1.2 molar, 10 μl). The extraction solution was then neutralized using 120 μl of a solution of 3-(N-morpholino)propanesulfonic acid buffer (2 molar) and ethylenediaminetetraacetic acid (25 mmolar, pH 7.5).

A nylon membrane, incorporated into a disposable device, was coated with succinylated casein (1.07 g/m²).

An IgG fraction from rabbit anti-serum to Streptococcus A (*Bacto Streptococcus* Antiserum, Group A, Lot #2672-50, from Difco Labs, Detroit, Mich.) was purified by precipitation with a 45% saturated ammonium sulfate solution followed by dialysis to remove the excess salt. The purified IgG fraction was then immobilized onto poly[styrene-co-m and p-(2-chloroethylsulfonylmethyl)styrene] beads (90:10 molar ratio) to give a dispersion of reagent (0.3% solids) in 0.05 molar glycine buffer (pH 8.5), containing 0.01% thimerosal as a preservative.

The purified IgG fraction was also conjugated to horseradish peroxidase (Sigma Chemical Co., St. Louis, Mo.) using succinimidyl 4-(N-maleimidomethyl)cyclohexane-1-carboxylate by a procedure similar to the method of Yoshitake et al (*Eur. J. Biochem.* 101, 395–399, 1979), then diluted to give a solution of the conjugate containing 9 μg/ml of IgG in 0.1% casein.

The bead suspension (40 μl) was added to the disposable, followed by the antigen extract (40 μl), 0.1% casein (120 μl) and conjugate (20 μl). The mixture was allowed to incubate on the membrane for 2 minutes at 25° C. The membrane was then washed with phosphate buffered saline solution (320 μl) and a dye-providing composition comprising the leuco dye 2-(4-hydroxy-3,5-dimethoxyphenyl)-4,5-bis(4-methoxyphenyl)imidazole (0.005 weight percent), sodium phosphate (5 mmolar, pH 6.8), polyvinylpyrolidone (1%), hydrogen peroxide (10 mmolar), 4'-hydroxyacetanilide (5 mmolar) and diethylenetriaminepentaacetic acid (10 mmolar) was added. After 3 minutes, a solution of sodium dodecylsulfate (0.1%, 80 μl) was added and the dye on the membrane was read by reflectance. The readings were converted to $D_T$ using the Williams-Clapper transform. Results are shown in the Table below as the averages of 2 or 3 tests for each level (colony forming units, CFU) of antigen.

TABLE

| CFU Group A Streptococcus | $D_T$ |
|---|---|
| $3 \times 10^5$ | 0.174 |
| $1.4 \times 10^5$ | 0.149 |
| $6.4 \times 10^4$ | 0.115 |
| $3.0 \times 10^4$ | 0.101 |
| $1.4 \times 10^4$ | 0.077 |
| $6.4 \times 10^3$ | 0.047 |
| No Cells (background) | 0.044 |

The invention has been described in detail with particular reference to preferred embodiments thereof, but it will be understood that variations and modifications can be effected within the spirit and scope of the invention.

We claim:

1. An aqueous dye-providing composition comprising a water-soluble or -dispersible polymer, an electron transfer agent, and an imidazole leuco dye which provides a dye in the presence of hydrogen peroxide and a peroxidative substance, the weight ratio of polymer to leuco dye being from about 10,000:1 to about 100:1, said polymer selected from the group consisting of vinylpyrrolidone polymers, acrylamide polymers, acrylic and methacrylic acid polymers, polyethylene glycols and polyamines.

2. The composition of claim 1 buffered to a pH of from about 6 to about 8.

3. The composition of claim 1 wherein said leuco dye is a triarylimidazole.

4. The composition of claim 3 wherein said triarylimidazole leuco dye has the formula:

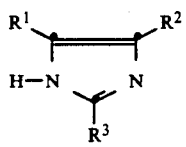

wherein $R^1$, $R^2$ and $R^3$ are each an organic group such that at least one of them is an ortho- or para-hydroxy substituted aryl group of up to 18 carbon atoms, the other two groups being aryl groups chosen such that the imidazole oxidation potential is between about $-70$ and $+110$ mV as measured by cyclic voltammetry against a standard calomel electrode using a carbon based electrode.

5. The composition of claim 1 further comprising hydrogen peroxide.

6. The composition of claim 1 further comprising a peroxidase labeled specific binding compound which will react specifically with another compound.

7. An aqueous dye-providing composition buffered to a pH of from about 6 to about 8 and comprising hydrogen peroxide, a phenolic electron transfer agent, poly(vinylpyrrolidone) and a triarylimidazole leuco dye which is selected from the group consisting of:
2-(4-hydroxy-3,5-dimethoxyphenyl)-4,5-bis(4-methoxyphenyl)imidazole,
2-(3,5-dibromo-4-hydroxyphenyl)-4,5-diphenylimidazole,
2-(3-bromo-5-methoxy-4-hydroxyphenyl)-4,5-bis(4-methoxyphenyl)imidazole,
4,5-bis(4-dimethylaminophenyl)-2-(4-hydroxyphenyl)imidazole,
4,5-bis(4-dimethylaminophenyl)-2-(4-hydroxy-3-methoxyphenyl)imidazole,
2-(4-hydroxyphenyl)-4,5-bis(4-methoxyphenyl)imidazole, and
4,5-bis(4-dimethylaminophenyl)-2-(4-hydroxy-3,5-dimethoxyphenyl)imidazole.

8. A diagnostic test kit for the determination of an analyte as a result of the catalytic activity of peroxidase, said kit comprising, separately packaged:
(a) a substrate for peroxidase, and
(b) an aqueous dye-providing composition comprising a water-soluble or -dispersible polymer, an electron transfer agent and an imidazole leuco dye which provides a dye in the presence of hydrogen peroxide and a peroxidative substance,
the weight ratio of polymer to leuco dye being from about 10,000:1 to about 100:1,
said polymer selected from the group consisting of vinylpyrrolidone polymers, acrylamide polymers, acrylic and methacrylic acid polymers, polyethylene glycols and polyamines.

9. The kit of claim 8 wherein said imidazole leuco dye has the formula:

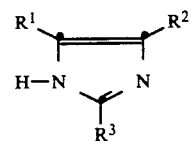

wherein $R^1$, $R^2$ and $R^3$ are each an organic group such that at least one of them is an ortho- or para-hydroxy substituted aryl group of up to 18 carbon atoms, the other two groups being aryl groups chosen such that the imidazole oxidation potential is between about $-70$ and $+110$ mV as measured by cyclic voltammetry against a standard calomel electrode using a carbon based electrode.

10. The kit of claim 8 further comprising a test device comprising a water-insoluble substrate having at least one test zone for carrying out an assay.

11. The kit of claim 8 further comprising a peroxidase labeled specific binding compound.

12. The kit of claim 11 wherein said specific binding compound is an antibody for human chorionic gonadotropin (hCG).

13. The kit of claim 8 further comprising a water-insoluble separation specific binding reagent.

14. The kit of claim 13 wherein said reagent comprises polymeric particles to which are bound avidin molecules.

15. The kit of claim 8 further comprising a biotinylated specific binding compound which will react specifically with another compound.

16. The kit of claim 8 wherein said polymer is a vinyl pyrrolidone homo- or copolymer.

17. A method for the determination of a ligand in an aqueous liquid, said method comprising:
A. contacting a sample of said liquid with a peroxidase labeled-receptor for said ligand to form a peroxidase labeled-reaction product of said ligand with said peroxidase labeled-receptor,
B. prior to, simultaneously with or subsequently to said contacting step (A), contacting said liquid sample with an aqueous dye-providing composition comprising a polymer, and an imidazole leuco dye which provides a dye in the presence of hydrogen peroxide and peroxidase,
said polymer selected from the group consisting of vinylpyrrolidone polymers, acrylamide polymers, acrylic and methacrylic acid polymers, polyethylene glycols and polyamines,
C. separating said peroxidase labeled-reaction product from unreacted materials, and
D. determining the presence or absence of said peroxidase labeled-reaction product by measuring the amount of dye associated with said reaction product, said amount being an indication of the amount of said ligand in said aqueous liquid.

18. The method of claim 17 for the determination of hCG in a urine sample wherein said peroxidase labeled-receptor is a peroxidase labeled-antibody to hCG.

19. The method of claim 17 wherein said triarylimidazole leuco dye has the formula:

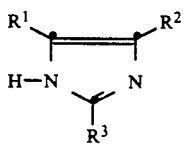

wherein R¹, R² and R³ are each an organic group such that at least one of them is an ortho- or para-hydroxy substituted aryl group of up to 18 carbon atoms, the other two groups being aryl groups chosen such that the imidazole oxidation potential is between about −70 and +110 mV as measured by cyclic voltammetry against a standard calomel electrode using a carbon based electrode.

20. A method for the determination of human chorionic gonadotropin (hCG) in an aqueous liquid, the method comprising the steps of:

A. contacting a sample of said liquid with a test device comprising a water-insoluble substrate having at least one test zone for carrying out said determination, and having immobilized in at least one of said test zones, a biotinylated antibody to hCG which is in dry form and admixed with a dried, water-soluble polymeric binder material, to form a reaction product of hCG with said biotinylated antibody at a first epitopic site, B. prior to, simultaneously with or subsequently to said contacting step (A), contacting said liquid sample with a second antibody to hCG which is labeled with peroxidase and which reacts with hCG at a second epitopic site, to form a peroxidase labeled-complex of hCG with said first and second antibodies, C. contacting said complex with a water-insoluble separation specific binding reagent comprising an insoluble phase to which avidin is bound, to form an insolubilized complex through reaction of avidin with biotin, D. prior to, simultaneously with or subsequently to said contacting step (C), contacting said complex with an aqueous dye-providing composition comprising a vinylpyrrolidone homo- or copolymer and an imidazole leuco dye which provides a dye in the presence of hydrogen peroxide and peroxidase, the weight ratio of polymer to leuco dye being from about 10,000:1 to about 100:1, E. separating the resulting peroxidase labeled, insolubilized complex from unreacted materials, and F. determining the presence or absence of said labeled, insolubilized complex by measuring the amount of dye associated with said complex, said amount being an indication of the amount of hCG in said aqueous liquid.

21. The method of claim 20 wherein said dye-providing composition is an aqueous composition buffered to a pH of from about 6 to about 8 and comprises a phenolic electron transfer agent, poly(vinylpyrrolidone) and a triarylimidazole leuco dye which is selected from the group consisting of:

2-(4-hydroxy-3,5-dimethoxyphenyl)-4,5-bis(4-methoxyphenyl)imidazole, 2-(3,5-dibromo-4-hydroxyphenyl)-4,5-diphenylimidazole, 2-(3-bromo-5-methoxy-4-hydroxyphenyl)-4,5-bis(4-methoxyphenyl)imidazole, 4,5-bis(4-dimethylaminophenyl)-2-(4-hydroxyphenyl)imidazole, 4,5-bis(4-dimethylaminophenyl)-2-(4-hydroxy-3-methoxyphenyl)imidazole, 2-(4-hydroxyphenyl)-4,5-bis(4-methoxyphenyl)imidazole, and 4,5-bis(4-dimethylaminophenyl)-2-(4-hydroxy-3,5-dimethoxyphenyl)imidazole.

* * * * *